United States Patent
Strelchenok (12)

(10) Patent No.: US 6,197,809 B1
(45) Date of Patent: Mar. 6, 2001

(54) COMPOUNDS FOR THE TREATMENT OF CANCER

(75) Inventor: Oleg Strelchenok, Minsk (BY)

(73) Assignee: Ardenia Investments Ltd. (GI)

( * ) Notice: Subject to any disclaimer, the term of this patent is extended or adjusted under 35 U.S.C. 154(b) by 0 days.

(21) Appl. No.: 09/471,301

(22) Filed: Dec. 23, 1999

(30) Foreign Application Priority Data

Dec. 23, 1998 (SE) .................................. 9804537
Mar. 11, 1999 (SE) .................................. 9900878
Mar. 16, 1999 (SE) .................................. 9900941

(51) Int. Cl.[7] .................. A61K 31/351; C07D 309/12
(52) U.S. Cl. ............................... 514/459; 549/417
(58) Field of Search ........................ 514/459; 549/417

(56) References Cited

U.S. PATENT DOCUMENTS 5,801,257 * 9/1998 Takeuchi et al. ............. 549/417

FOREIGN PATENT DOCUMENTS

WO 93/05774 4/1993 (WO) ..................... C07K/3/00

OTHER PUBLICATIONS

Vitols, et al.,"Selective Uptake of a Toxic Lipophilic Anthracycline Derivative by the Low–Density Lipoprotein Receptor Pathway in Cultured Fibroblasts," J. Med. Chem., vol. 28, 1985, pp. 451–454.

Sasaki, et al., "Daunomycin–Arachidonic Acid Complex As a Potential New Antitumor Agent," Cancer Chemotherapy Pharmacology, vol. 13, 1984, pp. 75–77.

Derwent Abstract, WO9618410 A1 960620 DW 9630.

Derwent Abstract, RU2097060 C1 971127 DW 9831.

* cited by examiner

*Primary Examiner*—Mukund J. Shah
*Assistant Examiner*—Hong Liu
(74) *Attorney, Agent, or Firm*—Morrison & Foerster LLP

(57) ABSTRACT

It is shown that the potency of anti-cancer drugs, here exemplified by doxorubicin, can be increased by the use of polyunsaturated fatty acid amides and in particular specific combinations of such compounds, forming complexes with doxorubicin. Further, a modified form of doxorubicin is presented.

5 Claims, No Drawings

COMPOUNDS FOR THE TREATMENT OF CANCER

FIELD OF THE INVENTION

This invention relates to new compounds, which are useful in the treatment of cancer. These compounds are used to increase the effect of conventional cytotoxic pharmaceuticals.

BACKGROUND OF THE INVENTION

Cytostatic or cytotoxic compounds are widely used in the treatment of cancer. Doxorubicin is an aminoglycosidic anthracycline antibiotic and will be used as a typical representative of this group of compounds.

The cell membrane represents a physical barrier and there are some factors that determine the rate of uptake of doxorubicin. The main factors are hydrophobicity (an increase will increase the rate of uptake) and protonation degree of amino group—pKa (a decrease will increase the rate of entry). The doxorubicin inhibits cell growth and has a marked effect on the nuclear material, which becomes non-specifically thickened, agglutinated or broken. The major binding force between doxorubicin and DNA is intercalation of the planar chromophore, stabilised by an external electrostatic binding of the positive charged amino sugar residue with negative phosphate group of DNA.

The intercalated drug molecules appear to prevent the changes in conformation of the helix, which are necessary as a preliminary to initiation of nucleic acid synthesis. The major lethal effect of doxorubicin is inhibition of nucleic acid synthesis. As consequence the drug is more active against dividing cells and the greatest effect is in the S stage of the cell cycle (Brown J. R., Adriamycin and related anthracycline antibiotics in: Progress in Medicinal Chemistry edited by G. P. Ellis and G. B. West, Elsevier/North-Holland Biomedical Press v.15, pp. 125–164, 1978).

Some observations are consistent with the formation complex of electrostatic nature between the positive amino group of doxorubicin and negative phosphate group of phospholipids such as cardiolipin, phosphatidyl serine, phosphatidyl inositol and phosphatidic acid. Cardiolipin is an almost characteristic component of the inner membrane of mitochondria, which are abundant in the cardiac muscle. The pathogenesis of the mitochondrial lesions is one of the major and more specific sub-cellular changes characterizing doxorubicin cardiotoxicity. The rather selective toxicity doxorubicin for mitochondria may be due to the high concentrations of cardiolipin in the mitochondria of the cardiac muscle (Duarte-Karim M., et al. Biochem. Biophys. Res. Comm., v.71, N.2, pp. 658–663, 1976).

The interaction between doxorubicin and lipids has been studied using large unilamellar vesicles (LUVET) composed of mixtures of anionic phospholipids and various zwitterionic phospholipids. Dilution of anionic lipids with zwitterionic lipids leads to decreased membrane association of the drug because electrostatic forces are very important in doxorubicin-membrane interaction. However, binding of doxorubicin to LUVET composed of anionic phospholipids combined with phosphatidylethanolamine (PE) is much higher than binding to LUVET made of anionic lipids plus a range of other zwitterionic lipids such as phosphatidylcholine and the N-methyethanolamine and N,N-dimethylethanolamine derivatives of PE (Speelmans G, et al., Biochemistry, v.36, N.28, pp. 8657–8662, 1997).

The interaction of adriamycin with human erythrocytes was investigated in order to determine the membrane binding sites and the resultant structural perturbation. Electron microscopy revealed that red blood cells incubated with the therapeutic concentration of the drug in human plasma changed their discoid shape to both stomatocytes and echinocytes. The drug was incubated with molecular models. One of them consisted of dimyristoylphosphatidylcholine and dimyristoylphosphatidylethanolamine multilayers, representatives of phospholipid classes located in the outer and inner leaflets of the erythrocyte membrane, respectively. X-ray diffraction showed that adriamycin interaction perturbed the polar head and acyl chain regions of both lipids. It is concluded that adriamycin incorporates into both erythrocyte leaflets affecting its membrane structure (Suwalsky M., Z Naturforsch [C] v.54, N3–4, pp. 271–277, 1999).

The different physicochemical properties of dipalmitoylphosphatidylcholine liposomes with soybean-derived sterols have been studied. Liposomal doxorubicin increased the pharmacological effect compared with free drug, suggesting a decrease of side effect and long circulation (Maitani Y., Yakugaku Zasshi, v.116, N.12, pp. 901–910, 1996).

Liposomes containing polyethylene glycol-derivatised phospholipids are able to evade the reticulo-endothelial system and thereby remain in circulation for prolonged periods. The doxorubicin encapsulated in these sterically stabilised liposomes suppresses the growth of established human lung tumour xenografts in severe combined immunodeficient mice and inhibits the spontaneous metastases of these tumours (Sakakibara T., et al., Cancer Res., v.56, N. 16, pp. 3743–3746, 1996).

A liposome encapsulation can protect surrounding tissue from the cytotoxic effects of the drugs after subcutaneous (s.c.) administration. Liposomes composed of "fluid-state" phospholipids only delayed the damaging effects of doxorubicin when injected s.c. Liposomes with a more rigid nature were much more effective in preventing local tissue damage over a longer period of time when administered s.c. (Oussoren C., et al., Biochim. Biophys. Acta, v.1369, N.1, pp. 159–172, 1998).

Exogenous polyunsaturated fatty acids modulate the cytotoxic activity of anti-cancer drugs in the human breast cancer cell line MDA-MB-231. Among all polyunsaturated fatty acids tested, docosahexaenoic acid was the most potent in increasing doxorubicin cytotoxicity (E. Germain, et al., Int. J. Cancer, v.75, pp. 578–583, 1998).

There remains a need for novel compounds and methods for the treatment of cancer. The present invention aims i.a. to increase the pharmacological activity of presently used anti-cancer drugs, such as doxorubicin, and to introduce novel approaches to the treatment of cancer.

SHORT SUMMARY OF THE INVENTION

The present invention makes available new compounds and new combinations of compounds, which, together with known cytotoxic or cytostatic pharmaceuticals, introduce improved possibilities to combat cancer. Further, the present invention discloses a method of synthesis of these compounds, and a modified form of a cytostatic pharmaceutical compound; doxorubicin.

DESCRIPTION OF THE INVENTION

It has been shown that the amount of lipoperoxides arise after the action of doxorubicin (DXR) in the presence of docosahexaenoic acid and oxidants, in the human breast cancer cells (line MDA-MB-231). This may endow tumour cells with metabolic characteristics that decrease their propensity to survive the effects of doxorubicin.

The present inventor has previously made available novel amides of the all-trans-retinoic acid or 13-cis-retinoic acid, arachidonic acid, docosahexaenoic acid and eicosapentaenoic acid or linolenic acid with 2-aminoehtanol, alpha-L-serine, alpha-L-threonine, alpha-L-tyrosine containing phosphate groups (SE 9900941-7, filed on Mar. 16, 1999). The present invention discloses the use of specific compounds, in particular their application for increase the pharmacological activity of doxorubicin.

These novel compounds contain hydrophobic residues of polyunsaturated fatty acids, retinoic acid residues and a phosphate group, which has a negative charge. Thus, the interaction between molecules of novel compounds and doxorubicin could be realised by hydrophobic interaction between fatty acid residues or retinoic acid residues and the planar chromophore of doxorubicin, as well as an electrostatic interaction between contrary charged functional groups both compounds.

On the one hand these binary complexes have all necessaries properties for directed transport through the membrane of the cancer cells and resemble a "Trojan horse". On the other hand, the dissociation of these binary complexes inside of the cancer cells releases "native", positive charged molecules of doxorubicin, with the result that favourable conditions for doxorubicin intercalation into DNA are created.

The following compounds 1 through 4, 1a through 4a, and 5 through 20 form the basis of the invention. They have—in part—been disclosed in the Swedish patent application no. 9900941-7, filed on Mar. 16, 1999.

Retinoic Acid Derivatives:
1. N-(all-trans-retinoyl)-o-phospho-2-aminoethanol
1a. N-(13-cis-retinoyl)-o-phospho-2-aminoethanol
2. N-(all-trans-retinoyl)-o-phospho-L-serine
2a. N-(13-cis-retinoyl)-o-phospho-L-serine
3. N-(all-trans-retinoyl)-o-phospho-L-threonine
3a. N-(13 -cis-retinoyl)-o-phospho-L-threonine
4. N-(all-trans-retinoyl)-o-phospho-L-tyrosine
4a. N-(13-cis-retinoyl)-o-phospho-L-tyrosine Arachidonic Acid Derivatives:
5. N-arachidonoyl-o-phospho-2-aminoethanol
6. N-arachidonoyl-o-phospho-L-serine
7. N-arachidonoyl-o-phospho-L-threonine
8. N-arachidonoyl-o-phospho-L-tyrosine Docosahexaenoic Acid Derivatives:
9. N-docosahexaenoyl-o-phospho-2-aminoethanol
10. N-docosahexaenoyl-o-phospho-L-serine
11. N-docosahexaenoyl-o-phospho-L-threonine
12. N-docosahexaenoyl-o-phospho-L-tyrosine Eicosapentaenoic Acid Derivatives:
13. N-eicosapentaenoyl-o-phospho-2-aminoethanol
14. N-eicosapentaenoyl-o-phospho-L-serine
15. N-eicosapentaenoyl-o-phospho-L-threonine
16. N-eicosapentaenoyl-o-phospho-L-tyrosine Linoleic Acid Derivatives:
17. N-linolenoyl-o-phospho-2-aminoethanol
18. N-linolenoyl-o-phospho-L-serine
19. N-linolenoyl-o-phospho-L-threonine
20. N-linolenoyl-o-phospho-L-tyrosine In the following description and examples, the above compounds are referred to as C1 through C4, C1a–C4a, and C5–C20.

A study of the anti-tumour effect of complexes between doxorubicin (DXR) and any one of the above compounds C1–C4, C1a–C4a, and C5–C20, as compared with DXR alone, was carried out using mice with EAC (Ehrlich ascites carcinoma). The extent of inhibition of EAC growth in mice, achieved by the tested compounds, compared to DXR, was used for evaluation of the anti-tumour activity of each tested DXR/compound complex.

It has been experimentally shown, that the complex DXR with any compound alone (C1–C4, C1a–C4a, and C5–C20) did not display an anti-tumour effect. In particular, in the DXR/C4 complex, the compound C4 cancelled the anti-tumour action of DXR and even exhibited some (insignificantly small) stimulating influence on EAC growth in mice. In the DXR/C5 complex, compound C5 cancelled the anti-tumour action of DXR.

The present inventor has however shown that complexes of DXR and C4 or C4a, together with C5; DXR/C4 (C4a) with C9; DXR/C4 (C4a) with C13; and DXR/C4 (C4a) with C17 display anti-tumour effects.

The attached series of experimental results, support this finding. The following doses were used:
DXR—3.5 mg/kg of body weight
C4—8.15 mg/kg of body weight At the molar ratios C4:C5 equal to 1:3; 1:2.9; 1:2.8; 1:2.7 and 1:2.6, the EAC growth inhibition was 45.0%; 43.6%; 46.0%; 48.2%; 50.4%, respectively.

At the molar ratios C4:C5: equal to 1:2.5; 1:2.4; 1:2.3 and 1:2.2, the EAC growth inhibition was 48.7%; 51.5%; 53.4% and 57.0%, respectively.

At the molar ratios C4:C5: equal to 1:2.1; 1:2; 1:1.9 and 1:1.8, the EAC growth inhibition was 58.0%; 59.5%; 62.0% and 65.2%, respectively.

At the molar ratios C4:C5 equal to 1:1.7; 1:1.6; 1:1.5 and 1:1.4, the EAC growth inhibition was 67.1%; 67.9%; 69.1% and 70.0%, respectively.

At the molar ratios C4:C5 equal to 1:13; 1:1.2; 1:1.1 and 1:1, the EAC growth inhibition was 69.4%; 66.7%; 62.5% and 65.2%, respectively.

It should be noted that, at the molar ratios C4:C5 equal to 1:1.7; 1:1.6; 1:1.5; 1:1.4 and 1:1.3, the EAC growth inhibition with reference to the DXR group (positive control) was 38.8%; 40.3%; 42.6%; 44.2% and 41.1%, respectively.
DXR—3.5 mg/kg of body weight
CS—6.4 mg/kg of body weight At the molar ratios C4:C5 equal to 1:1; 1.1:1; 1.2:1; 1.3:1 and 1.4:1, the EAC growth inhibition was 65.2%; 61.6%; 66.2%; 69.3% and 69.8%, respectively.

At the molar ratios C4:C5 equal to 1.5:1; 1.6:1; 1.7:1 and 1.8:1, the EAC growth inhibition was 74.9%; 78.1%; 74.1% and 66.4%, respectively.

At the molar ratios C4:C5 equal to 1.9:1; 2:1; 2.1:1 and 2.2:1, the EAC growth inhibition was 65.1%; 61.8%; 63.2% and 58.0%, respectively.

At the molar ratios C4:C5 equal to 2.3:1; 2.4:1; 2.5:1 and 2.6:1, the EAC growth inhibition was 55.5%; 58.7%; 56.7% and 57.6%, respectively.

At the molar ratios C4:C5 equal to 2.7:1; 2.8:1; 2.9:1 and 3:1, the EAC growth inhibition was 56.6%; 55.0%; 50.4% and 45.3%, respectively.

It should be noted that, at the molar ratios C4:C5 equal to 1.3:1; 1.4:1; 1.5:1; 1.6:1 and 1.7:1, the EAC growth inhibition with reference to the DXR group (positive control) was 43.2%; 44.1%; 51.4%; 57.7% and 49.8%, respectively.

In particular, some of the experiments for testing the anti-tumour effects of DXR/C4+C9 complexes, DXR/C4+C13 complexes, DXR/C4+C17 complexes, DXR/C4a+C5 complexes indicate this.

DXR/C4+C9 Complexes:

DXR—3.5 mg/kg of body weight, and C4—8.15 mg/kg of body weight

At the molar ratios C4:C9 equal to 1:1; 1:1.4; 1:1.8 and 1:2.3, the EAC growth inhibition was 61.8%; 67.3%; 62.5% and 49.7%, respectively.

At the molar ratio C4:C9 equal to 1:1.4, the EAC growth inhibition with reference to the DXR group (positive control) was 49.3%.

DXR/C4+C13 Complexes:

DXR—3.5 mg/kg of body weight, and C4—8.15 mg/kg of body weight.

At the molar ratios C4:C13 equal to 1:1.3; 1:1.6; 1:2 and 1:2.5, the EAC growth inhibition was 67.0%; 64.6%; 54.2% and 45.1%, respectively.

At the molar ratios C4:C13 equal to 1:1.3 and 1:1.6, the EAC growth inhibition with reference to the DXR group (positive control) was 47.6% and 43.8%, respectively.

DXR/C4+C17 Complexes:

DXR—3.5 mg/kg of body weight, and C17—6,0 mg/kg of body weight.

At the molar ratios C4:C17 equal to 1:1; 1.4:1; 2:1 and 2.7:1, the EAC growth inhibition was 62.9%; 67.4%; 60.3% and 51.8%, respectively.

At the molar ratio C4:C17 equal to 1.4:1, the EAC growth inhibition with reference to the DXR group (positive control) was 45.0%.

DXR/C4a+C5 Complexes:

DXR—3.5 mg/kg of body weight, and C5—6,4 mg/kg of body weight.

At the molar ratios C4a:C5 equal to 1.2:1; 1.6:1; 1.9:1 and 2.5:1, the EAC growth inhibition was 64.4%; 72.4%; 62.2% and 52.5%, respectively.

At the molar ratio C4a:C5 equal to 1.6:1, the EAC growth inhibition with reference to the DXR group (positive control) was 49.4%.

The present inventor has shown that DXR/(C4+C4a)+C5 complexes; DXR/(C4+C4a)+(C5+C9+C13) complexes; DXR/(C4+C4a)+(C5+C9+C13+C17) complexes display an anti-tumour effect. The experiments for testing the anti-tumour effect support this finding.

DXR/(C4+C4a)+C5 complexes: DXR—3.5 mg/kg of body weight

C5—6.4 mg/kg of body weight

At the molar ratios (C4+C4a):C5 equal to 1.2:1; 1.6:1; 1.9:1 and 2.5:1 EAC growth inhibition was 63.1%; 71.6%; 61.0% and 47.3%, respectively.

At the molar ratios (C4+C4a):C5 equal to 1.6:1 EAC growth inhibition with reference to DXR group (positive control) was 53.1%.

DXR/(C4+C4a)+(C5+C9+C13) complexes: DXR—3.5 mg/kg of body weight (C4+C4a)—8.15 mg/kg of body weight At the molar ratios (C4+C4a):(C5+C9+C13) equal to 1:1; 1:1.4; 1:1.8 and 1:2.3 EAC growth inhibition was 60.1%; 68.3%; 61.3% and 47.2%, respectively.

At the molar ratios (C4+C4a):(C5+C9+C13) equal to 1:1.4 EAC growth inhibition with reference to DXR group (positive control) was 49.8%.

DXR/(C4+C4a)+(C5+C9+C13+C17) complexes: DXR—3.5 mg/kg of body weight (C4+C4a)—8.15 mg/kg of body weight At the molar ratios (C4+C4a):(C5+C9+C13+C17) equal to 1:1.3; 1:1.6; 1:2 and 1:2.5 EAC growth inhibition was 68.0%; 69.7%; 56.3% and 43.5%, respectively.

At the molar ratios (C4+C4a):(C5+C9+C13+C17) equal to 1:1.3 and 1:1.6 EAC growth inhibition with reference to DXR group (positive control) was 45.3% and 48.1% respectively.

Investigations of the anti-tumour effects of DXR/C4+C5 complexes, DXR/C4+C9 complexes, DXR/C4+C13 complexes, DXR/C4+C17 complexes, DXR/C4a+C5 complexes allow the following conclusion:

At the molar ratios C4(or C4a):C5 (or C9 or C13 or C17) from 1:3 to 1:1 and from 1:1 to 3:1, the anti-tumour action complexes exceed the effect of DXR alone. The results show significant effects for complexes within the intervals 1:2–1:1 and 1:1–2:1, with improved effects corresponding to the more narrow intervals 1:1.7–1:1.3 and 1.3:1–1.7:1.

The investigation of anti-tumour effects of DXR/(C4+C4a)+C5 complexes, DXR/(C4+C4a)+(C5+C9+C13) complexes, DXR/(C4+C4a)+(C5+C9+C13+C17) complexes confirm this conclusion. Moreover, it is true for complexes, in which from two to six compounds (4, 4a, 5, 9, 13, 17) participate in interactions with DXR.

These results were obtained at such concentrations of novel compounds (C4, C4a, C5, C9, C13, C17) which are considerably above their critical micelle concentrations.

A water-soluble aromatic compound, such as doxorubicin could be in the form of micelle in water solutions. The present inventor has surprisingly found, that doxorubicin in a concentration interval of 1–2 mg/ml forms mixed micelles with the novel compounds (C4, C4a, C5, C9, C13, C17) more effectively. Further, the anti-tumour activity of these mixed micelles is significantly higher then for doxorubicin alone in the same concentrations.

Thus, mixed micelles consisting of an amide of the all-trans-retinoic acid or/and an amide of the 13-cis-retinoic acid with O-phospho-L-tyrosine (C4 or C4a; C4+C4a), amides of polyunsaturated acids with O-phosphorylethanolamine (C5 or C9 or C13 or C17; C5+C9; C5+C13; C5+C17; C9+C13; C9+C17; C13+C17; C5+C9+C13; C5+C9+C17; C5+C13+C17; C9+C13+C17; C5+C9+C13+C17) and doxorubicin, display anti-tumour activity.

Thus, mixed micelles consisting of amide of the all-trans-retinoic acid or 13-cis-retinoic acid with O-phospho-L-tyrosine (C4 or C4a), amide polyunsaturated acid with O-phosphorylethanolamine (C5 or C9 or C13 or C17) and doxorubicin, display anti-tumour activity.

The inventor has previously described a universal method of synthesis amides of retinoic acids and polyunsaturated acids with hydroxyamino acids and ethanolamine containing phosphate groups. In the present application, the inventor discloses a method of synthesis of the N-acyl-O-phospho-2-aminoethanol and the N-retinoyl-O-phospho-L-tyrosine.

That method has the following advantages in comparison with previous one the synthesis is performed in one step the yield is high, reaching 90%, simplified and time-saving synthesis the final product can be purified without chromatography

EXAMPLES

Materials and Methods:

The study of the anti-tumour effects of complexes between doxorubicin and compound 4 (C4) or compound 4a (C4a) and compound 5 (CS) or compound 9 (C9) or compound 13 (C13) or compound 17 (C17) as compared to doxorubicin (DXR) was carried out in mice with Ehrlich ascites carcinoma (EAC). Random-bred albino mice of line ICR, male and female, from own rearing were used in the study. The room for animal housing was provided with filtered air at 15 changes per hour, a temperature of 19–21° C., relative humidity of 50–60% and regulated light day of 12 hours with change of light and darkness at 6 a.m. and 6 p.m. The mice were kept in transparent polycarbonate cages with a floor area of 600 cm² containing softwood sawdust bedding. The animals had free access to bottles with domestic quality drinking tap water and to standard feeding for growing animals ad libidum. The mice aged 2–2.5 months and having a weight of 19–22 g were randomly distributed in the control and test groups, standardised by mean weights. The control and test groups included 10 and 7 animals correspondingly. The mice of each group were identified by specific ear marks. The cages with animals of each group were identified by cage cards marked with the study date, group number, number and sex of the animals.

The strain of EAC was propagated in ICR mice by intraperitoneal inoculation of 0.2 ml native ascites fluid or 0.5 ml ascites fluid diluted by saline to 1:1 from one or two animals with intraperitoneally growing EAC on day 7. Ascites fluids contained more 98% of viable tumour cells accordig to trypan blue exclusion test. For the each study the suspension of EAC cells in sterile saline in concentration of $10^7$ viable tumour cells/ml was prepared in aseptic conditions from ascites fluid of mouse bearing of EAC on day 7.

The mice of each control and experimental groups were inoculated by intraperitoneal injection of $2 \times 10^6$ EAC cells in volume of 0.2 ml at day 0. Intravenous injections for the study were carried out in lateral tail vein of mice once every other day, three times (day 2, 4 and 6) following inoculation of EAC cells. The mice of control group were injected by vehicle in volume of 2.5 ml/kg of body weight (50 µl to mouse of 20 g body weight) intravenously (negative control). Other group of animals (positive control) received water solution of DXR (in concentration of 1.4 mg/ml) in the dose of 3.5 mg/kg of body weight and in volume of 2.5 ml/kg of body weight (70 µg of DXR in 50 µl to mouse of 20 g body weight) intravenously. The mice of test groups were injected intravenously by complexes of DXR/C4+C5 (two series of experiments); complexes of DXR/C4+C9 (some experiments); complexes of DXR/C4+C13 (some experiments); complexes of DXR/C4+C17 (some experiments); complexes of-DXR/C4a+C5 (some experiments). The mice of test groups received the DXR (in complexes) in the dose of 3.5 mg/kg of body weight and in volume of 2.5 ml/kg of body weight (corresponding to 70 µg of DXR in 50 µl to mouse of 20 g body weight); concentration of DXR 1,4 mg/ml. One series of experiments was designated to study the anti-tumour effect of complexes of DXR/C4+C5 at constant content of C4 (8.15 mg/kg of body weight) but at different content of C5 with molar ratio C4:C5, varying from 1:3 to 1:1. Other series of experiments was designated to study the anti-tumour effect of complexes of DXR/C4+C5 at constant content of C5 (6.4 mg/kg of body weight) but at different content of C4 with molar ratio C4:C5, varying from 1:1 to 3:1. Solutions of complexes and doxorubicin were injected strictly intravenously as occasional partial subcutaneous injection can lead to pain reaction of animal, local irritant damage, or ulceration and necrosis at times.

The mice were killed by cervical dislocation two days later after the final treatment with the test complexes on day 8. Ascites fluids were removed, collected, their volumes were recorded, and abdominal cavities were washed by saline 6–7 times and both fluids were pooled. After centrifugation at 1000 r.p.m. for 10 min volumes of tumour cell pellet were also recorded. Number of viable tumour cells was counted by hemocetometer. Means and standard errors for each groups were calculated. Comparison of tumour cell number in control and test groups was carried out using Student's t-test. The influence of tested preparations on EAC growth inhibition was evaluated by the following formula:

$$\text{inhibition } \% = \frac{\text{Control} - \text{Test}}{\text{Control}} \times 100$$

The extent of inhibition of EAC growth in mice, affected by the test preparations compared to DXR, was used for evaluation of anti-tumour activity of tested complexes.

Example 1
Anti-tumour Effect of DXR/C4 Complex

Mice ICR of 20–22 g were inoculated intraperitoneally with $2 \times 10^6$ viable EAC cells. Starting two days later (day 2) mice were injected intravenously (in the volume of 2.5 ml/kg of body weight) once every other day, three times (day 2, 4 and 6). Mice of control group received vehicle. In the group of DXR mice received DXR alone in the dose of 3.5 mg/kg. Mice of test group received the complex of DXR/C4 (DXR—3.5 mg/kg; C4—22.5 mg/kg). Two days later after the final treatment with test complex mice were killed by cervical dislocation on day 8. Tumour cell number was counted and the extent of inhibition of EAC growth in mice was evaluated.

Mice of control group had $(680.0 \pm 59.1) \times 10^6$ EAC cells in abdominal cavity. In the group receiving DXR alone, the number of tumour cells was $(510.9 \pm 52.9) \times 10^6$ and EAC growth inhibition 24,9%, p<0.05. In mice in the test group receiving the DXR/C4 complex, the number of tumour cells was $(787.2 \pm 141.8) \times 10^6$, p>0.05.

Thus, the DXR/C4 complex did not display an anti-tumour action. Moreover, compound 11 canceled the anti-tumour action of DXR and exerted insignificantly some stimulating influence on EAC growth in mice with reference to negative control.

Example 2
Anti-tumour Effect of DXR/C5 Complex

Mice ICR of 20–22 g were inoculated intraperitoneally with $2 \times 10^6$ viable EAC cells. Starting two days later (day 2) mice were injected intravenously (in the volume of 2.5 ml/kg of body weight) once every other day, three times (day 2, 4 and 6). Mice of control group received vehicle. In the group of DXR mice received DXR alone in the dose of 3.5 mg/kg. Mice of test group received the DXR/C5 complex (DXR—3.5 mg/kg; C5—12 mg/kg). Two days later after the final treatment with test complex mice were killed by cervical dislocation on day 8. Tumour cell number was counted and the extent of inhibition of EAC growth in mice was evaluated.

Mice of control group had $(680.0 \pm 59.1) \times 10^6$ EAC cells in abdominal cavity. In group with DXR alone the number of tumour cells was $(510.9 \pm 52.9) \times 10^6$ and EAC growth inhibition of 24,9%, p<0.05. In mice of test group with DXR/C5 complex the number of tumour cells was $(635.6 \pm 122.2) \times 10^6$, p>0.05.

Thus, the DXR/C5 complex did not display an anti-tumour action. Moreover, C5 canceled the anti-tumour action of DXR.

Series of experiments for testing of anti-tumour effect of DXR/C4+C5 complexes. DXR—3.5 mg/kg of body weight. C4—8.15 mg/kg of body weight. C4:C5 molar ratio varied from 1:3 to 1:1.

Example 3
The anti-tumour Effect of DXR/C4+C5 complexes, the C4:C5 Molar Ratios Being Equal to 1:3; 1:2,9; 1:2.8; 1:2.7 and 1:2.6

ICR-mice weighing 20–22 g were inoculated intraperitoneally with $2 \times 10^6$ viable EAC cells. Starting two days later (day 2), the mice were injected intravenously (with a volume corresponding to 2.5 ml/kg body weight) once every other day, three times (day 2, 4 and 6). Mice of control group received only vehicle. In the group of DXR mice received DXR alone in the dose of 3.5 mg/kg. Mice of first test group received the DXR/C4+C5 complex (C4:C15 molar ratio was equal to 1:3). Mice of second test group received the DXR/C4+C5 complex (C4:C5 molar ratio was equal to 1:2.9). Mice of third test group received the DXR/C4+C5 complex (C4+C5 molar ratio was equal to 1:2.8). Mice of fourth test group received the DXR/C4+C5 complex (C4:C5 molar ratio was equal to 1:2.7). Mice of fifth test group received the DXR/C4+C5 complex (C4:C5 molar ratio was equal to 1:2.6). Two days later after the final treatment with the test complexes mice were killed by cervical dislocation on day 8. Tumour cell number was counted and the extent of inhibition of EAC growth in mice was evaluated.

Mice of control group had $(657.5\pm72.6)\times10^6$ EAC cells in abdominal cavity. In group with DXR alone the number of tumour cells was $(407.4\pm75.9)\times10^6$ and EAC growth inhibition of 38.0%, $p<0.05$. In mice of first test group the number of tumour cells was $(361.3\pm98.5)\times10^6$ and EAC growth inhibition of 45.0%, $p<0.05$. In mice of second test group the number of tumour cells was $(370.6\pm94.9)\times10^6$ and EAC growth inhibition of 43.6%, $p<0.05$. In mice of third test group the number of tumour cells was $(354.9\pm101.2)\times10^6$ and EAC growth inhibition of 46.0%, $p<0.05$. In mice of fourth test group the number of tumour cells was $(340.8\pm104.7)\times10^6$ and EAC growth inhibition of 48.2%, $p<0.05$. In mice of fifth test group the number of tumour cells was $(326.1\pm93.3)\times10^6$ and EAC growth inhibition of 50.4%, $p<0.05$.

Thus, the anti-tumour activity of DXR/C4+C5 complexes at various C4:C5 molar ratios from 1:3.0 to 1:2.6 exceeds the effect of DXR alone.

Example 4

The Anti-tumour Effect of DXR/C4+C5 Complexes, the C4:C5 Molar Ratios Being Equal to 1:2.5; 1:2.4; 1:2.3 and 1:2.2

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 1:2.5). Mice of second test group received the DXR/C4+C5 complex (C4:C5 molar ratio was equal to 1:2.4). Mice of third test group received the DXR/C4+C5 complex (C4:C5 molar ratio was equal to 1:2.3). Mice of fourth test group received the DXR/C4+C5 complex (C4:C5 molar ratio was equal to 1:2.2). Two days later after the final treatrnent with the test complexes mice were killed by cervical dislocation on day 8. Tumour cell number was counted and the extent of inhibition of EAC growth in mice was evaluated.

Mice of control group had $(935.1\pm107.8)\times10^6$ EAC cells in abdominal cavity. In group with DXR alone the number of tumour cells was $(548.5\pm81.7)\times10^6$ and EAC growth inhibition of 41.3%, $p<0.02$. In mice of first test group the number of tumour cells was $(479.4\pm103.8)\times10^6$ and EAC growth inhibition of 48.7%, $p<0.01$. In mice of second test group the number of tumour cells was $(453.7\pm125.1)\times10^6$ and EAC growth inhibition of 51.5%, $p<0.02$. In mice of third test group the number of tumour cells was $(435.5\pm99.8)\times10^6$ and EAC growth inhibition of 53.4%, $p<0.01$. In mice of fourth test group the number of tumour cells was $(402.0\pm116.9)\times10^6$ and EAC growth inhibition of 57.0%, $p<0.01$.

Thus, anti-tumour activity of DXR/C4+C5 complexes at various molar C4:C5 ratios from 1:2.5 to 1:2.2 exceeds the effect of DXR alone.

Example 5

The Anti-tumour Effect of DXR/C4+C5 Complexes, the C4:C5 Molar Ratios Being Equal to 1:2.1; 1:2; 1:1.9 and 1:1.8

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 1:2.1). Mice of second test group received the DXR/C4+C5 complex (C4:C5 molar ratio was equal to 1:2). Mice of third test group received the DXR/C4+C5 complex (C4:C5 molar ratio was equal to 1:1.9). Mice of fourth test group received the DXR/C4+C5 complex (C4:C5 molar ratio was equal to 1:1.8). Two days later after the final treatment with the test complexes mice were killed by cervical dislocation on day 8. Tumour cell number was counted and the extent of inhibition of EAC growth in mice was evaluated.

Mice of control group had $(862.4\pm125.0)\times10^6$ EAC cells in abdominal cavity. In group with DXR alone the number of tumour cells was $(455.3\pm131.3)\times10^6$ and EAC growth inhibition of 47.2%, $p<0.05$. In mice of first test group the number of tumour cells was $(361.8\pm79.4)\times10^6$ and EAC growth inhibition of 58.0%, $p<0.01$. In mice of second test group the number of tumour cells was $(349.3\pm92.2)\times10^6$ and EAC growth inhibition of 59.5%, $p<0.01$. In mice of third test group the number of tumour cells was $(327.5\pm108.6)\times10^6$ and EAC growth inhibition of 62.0%, $p<0.01$. In mice of fourth test group the number of tumour cells was $(300.2\pm84.7)\times10^6$ and EAC growth inhibition of 65.2%, $p<0.01$.

Thus, anti-tumour activity of DXR/C4+C5 complexes at various C4:C5 molar ratios from 1:2.1 to 1:1.8 exceeds the effect of DXR alone.

Example 6

The Anti-tumour Effect of DXR/C4+C5 Complexes, the C4:C5 Molar Ratios Being Equal to 1:1.7; 1:1.6; 1:1.5 and 1:1.4

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg, Mice of first test group received the DXR/C4+C5 complex (C4:C5 molar ratio was equal to 1:1.7). Mice of second test group received the DXR/C4+C5 complex (C4:C5 molar ratio was equal to 1:1.6). Mice of third test group received the DXR/C4+C5 complex (C4:C5 molar ratio was equal to 1:1.5). Mice of fourth test group received the DXR/C4+C5 complex (C4:C5 molar ratio was equal to 1:1.4). Two days later after the final treatment with the test complexes mice were killed by cervical dislocation on day 8. Tumour cell number was counted and the extent of inhibition of EAC growth in mice was evaluated.

Mice of control group had $(779.1\pm76.7)\times10^6$ EAC cells in abdominal cavity. In group with DXR alone the number of tumour cells was $(419.0\pm53.4)\times10^6$ and EAC growth inhibition of 46.2%, $p<0.002$. In mice of first test group the number of tumour cells was $(256.3\pm54.1)\times10^6$ and EAC growth inhibition of 67.1%, p<0.001, and with reference to DXR group (positive control) EAC growth inhibition of 38.8%, p<0.05. In mice of second test group the number of tumour cells was $(250.1\pm57.7)\times10^6$ and EAC growth inhibition of 67.9%, p<0.001, and with reference to DXR group (positive control) EAC growth inhibition of 40.3%, p<0.05. In mice of third test group the number of tumour cells was $(240.7\pm61.8)\times10^6$ and EAC growth inhibition of 69.1%, p<0.001, and with reference to DXR group (positive control) EAC growth inhibition of 42.6%, p<0.05. In mice of fourth test group the number of tumour cells was $(233.7\pm50.8)\times10^6$ and EAC growth inhibition of 70.0%, p<0.001, and with reference to DXR group (positive control) EAC growth inhibition of 44.2%, p<0.05.

Thus, the anti-tumour activity of DXR/C4+C5 complexes at various C4:C5 molar ratios from 1:1.7 to 1:1.4 exceeds the effect of DXR alone.

Example 7

The Anti-tumour Effect of DXR/C4+C5 Complexes, the C4:C5 Molar Ratios Being Equal to 1:1.3; 1:1.2; 1:1.1 and 1:1

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 1:1.3). Mice of second test group received the DXR/C4+C5 complex (C4:C5 molar ratio was equal to 1:1.2). Mice of third test group received the DXR/C4+C5 complex (C4:C5 molar ratio was equal to 1:1.1). Mice of fourth test group received the DXR/C4+C5 complex (C4:C5 molar ratio was equal to 1:1). Two days later after the final treatment with the test complexes mice were killed by cervical dislocation on day 8. Tumour cell number was counted and the extent of inhibition of EAC growth in mice was evaluated.

Mice of control group had $(793.4\pm72.8)\times10^6$ EAC cells in abdominal cavity. In group with DXR alone the number of tumour cells was $(411.9\pm57.1)\times10^6$ and EAC growth inhibition of 48.1%, p<0.02. In mice of first test group the number of tumour cells was $(242.6\pm54.3)\times10^6$ and EAC growth inhibition of 69.4%, p<0.001, and with reference to DXR group (positive control) EAC growth inhibition of 41.1%, p<0.05. In mice of second test group the number of tumour cells was $(264.1\pm87.6)\times10^6$ and EAC growth inhibition of 66.7%, p<0.001. In mice of third test group the number of tumour cells was $(297.7\pm94.3)\times10^6$ and EAC growth inhibition of 62.5%, p<0.001. In mice of fourth test group the number of tumour cells was $(276.1\pm76.5)\times10^6$ and EAC growth inhibition of 65.2%, p<0.001.

Thus, anti-tumour activity of DXR/C4+C5 complexes at various C4:C5 molar ratios from 1:1.3 to 1:1 exceeds the effect of DXR alone.

Series of experiments for testing of anti-tumour effect of DXR/C4+C5 complexes. DXR—3.5 mg/kg of body weight. C5—6.4 mg/kg of body weight. C4:C5 molar ratio varied from 1:1 to 3:1.

Example 8

The Anti-tumour Effect of DXR/C4+C5 Complexes, the C4:C5 Molar Ratios Being Equal to 1:1; 1.1:1; 1.2:1; 1.3:1 and 1.4:1

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 1:1). Mice of second test group received the DXR/C4+C5 complex (C4:C5 molar ratio was equal to 1.1:1). Mice of third test group received the DXR/C4+C5 complex (C4:C5 molar ratio was equal to 1.2:1). Mice of fourth test group received the DXR/C4+C5 complex (C4:C5 molar ratio was equal to 1.3:1). Mice of fifth test group received the DXR/C4+C5 complex (C4:C5 molar ratio was equal to 1.4:1). Two days later after the final treatment with the test complexes mice were killed by cervical dislocation on day 8. Tumour cell number was counted and the extent of inhibition of EAC growth in mice was evaluated.

Mice of control group had $(742.2\pm66.2)\times10^6$ EAC cells in abdominal cavity. In group with DXR alone the number of tumour cells was $(400.3\pm63.5)\times10^6$ and EAC growth inhibition of 46.1%, p<0.001. In mice of first test group the number of tumour cells was $(258.3\pm40.4)\times10^6$ and EAC growth inhibition of 65.2%, p<0.001. In mice of second test group the number of tumour cells was $(284.8\pm97.5)\times10^6$ and EAC growth inhibition of 61.6%, p<0.002. In mice of third test group the number of tumour cells was $(251.2\pm103.6)\times10^6$ and EAC growth inhibition of 66.2%, p<0.001. In mice of fourth test group the number of tumour cells was $(227.5\pm43.3)\times10^6$ and EAC growth inhibition of 69.3%, p<0.001, and with reference to DXR group (positive control) EAC growth inhibition of 43.2%, p<0.05. In mice of fifth test group the number of tumour cells was $(223.8\pm43.2)\times10^6$ and EAC growth inhibition of 69.8%, p<0.001, and with reference to DXR group (positive control) EAC growth inhibition of 44.1%, p<0.05.

Thus, anti-tumour activity of DXR/C4+C5 complexes at various C4:C5 molar ratios from 1:1 to 1.4:1 exceeds the effect of DXR alone.

Example 9

The Anti-tumour Effect of DXR/C4+C5 Complexes, the C4:C5 Molar Ratios Being Equal to 1.5:1; 1.6:1; 1.7:1 and 1.8:1

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 1.5:1). Mice of second test group received the DXR/C4+C5 complex (C4:C5 molar ratio was equal to 1.6:1). Mice of third test group received the DXR/C4+C5 complex (C4:C5 molar ratio was equal to 1.7:1). Mice of fourth test group received the DXR/C4+C5 complex (C4:C5 molar ratio was equal to 1.8:1). Two days later after the final treatment with the test complexes mice were killed by cervical dislocation on day 8. Tumour cell number was counted and the extent of inhibition of EAC growth in mice was evaluated.

Mice of control group had $(953.5\pm167.3)\times10^6$ EAC cells in abdominal cavity. In group with DXR alone the number of tumour cells was $(492.1\pm85.3)\times10^6$ and EAC growth inhibition of 48.4%, p<0.05. In mice of first test group the number of tumour cells was $(239.3\pm93.5)\times10^6$ and EAC growth inhibition of 74.9%, p<0.002, and with reference to DXR group (positive control) EAC growth inhibition of 51.4%, p<0.05. In mice of second test group the number of tumour cells was $(208.4\pm89.0)\times10^6$ and EAC growth inhibition of 78.1%, p<0.002, and with reference to DXR group (positive control) EAC growth inhibition of 57.7%, p<0.05. In mice of third test group the number of tumour cells was $(247.1\pm76.8)\times10^6$ and EAC growth inhibition of 74.1%, p<0.002, and with reference to DXR group (positive control) EAC growth inhibition of 49.8%, p<0.05. In mice of fourth test group the number of tumour cells was $(320.4\pm120.6)\times10^6$ and EAC growth inhibition of 66.4%, p<0.01.

Thus, the anti-tumour activity of DXR/C4+C5 complexes at various C4:C5 molar ratios from 1.5:1 to 1.8:1 exceeds the effect of DXR alone.

Example 10
The Anti-tumour Effect of DXR/C4+C5 Complexes, the C4:C5 Molar Ratios Being Equal to 1.9:1; 2:1; 2.1:1 and 2.2:1

Mice ICR of 20–22 g were inoculated intraperitoneally with $2\times10^6$ viable EAC cells. Starting two days later (day 2) mice were injected intravenously (in the volume of 2.5 ml/kg of body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 1.9:1). Mice of second test group received the DXR/C4+C5 complex (C4:C5 molar ratio was equal to 2:1). Mice of third test group received the DXR/C4+C5 complex (C4:C5 molar ratio was equal to 2.1:1). Mice of fourth test group received the DXR/C4+C5 complex (C4:C5 molar ratio was equal to 2.2:1). Two days later after the final treatment with the test complexes mice were killed by cervical dislocation on day 8. Tumour cell number was counted and the extent of inhibition of EAC growth in mice was evaluated.

Mice of control group had $(924.6\pm145.2)\times10^6$ EAC cells in abdominal cavity. In group with DXR alone the number of tumour cells was $(481.0\pm105.3)\times10^6$ and EAC growth inhibition of 48.0%, p<0.01. In mice of first test group the number of tumour cells was $(322.8\pm93.5)\times10^6$ and EAC growth inhibition of 65.1%, p<0.01. In mice of second test group the number of tumour cells was $(353.2\pm74.4)\times10^6$ and EAC growth inhibition of 61.8%, p<0.01. In mice of third test group the number of tumour cells was $(340.3\pm86.8)\times10^6$ and EAC growth inhibition of 63.2%, p<0.01. In mice of fourth test group the number of tumour cells was $(388.3\pm91.6)\times10^6$ and EAC growth inhibition of 58.0%, p<0.01.

Thus, the anti-tumour activity of DXR/C4+C5 complexes at various C4:C5 molar ratios from 1.9:1 to 2.2:1 exceeds the effect of DXR alone.

Example 11
The Anti-tumour Effect of DXR/C4+C5 Complexes, the C4:C5 Molar Ratios Being Equal to 2.3:1; 2.4:1; 2.5:1 and 2.6:1

Mice ICR of 20–22 g were inoculated intraperitoneally with $2\times10^6$ viable EAC cells. Starting two days later (day 2) mice were injected intravenously (in the volume of 2.5 ml/kg of body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 2.3:1). Mice of second test group received the DXR/C4+C5 complex (C4:C5 molar ratio was equal to 2.4:1). Mice of third test group received the DXR/C4+C5 complex (C4:C5 molar ratio was equal to 2.5:1). Mice of fourth test group received the DXR/C4+C5 complex (C4:C5 molar ratio was equal to 2.6:1). Two days later after the final treatment with the test complexes mice were killed by cervical dislocation on day 8. Tumour cell number was counted and the extent of inhibition of EAC growth in mice was evaluated.

Mice of control group had $(857.6\pm113.9)\times10^6$ EAC cells in abdominal cavity. In group with DXR alone the number of tumour cells was $(525.2\pm104.5)\times10^6$ and EAC growth inhibition of 38.8%, p<0.05. In mice of first test group the number of tumour cells was $(381.4\pm64.8)\times10^6$ and EAC growth inhibition of 55.5%, p<0.01. In mice of second test group the number of tumour cells was $(354.2\pm78.1)\times10^6$ and EAC growth inhibition of 58.7%, p<0.01. In mice of third test group the number of tumour cells was $(371.4\pm136.5)\times10^6$ and EAC growth inhibition of 56.7%, p<0.02. In mice of fourth test group the number of tumour cells was $(363.7\pm158.4)\times10^6$, inhibition of EAC growth was 57.6%, p<0.05.

Thus, the anti-tumour activity of DXR/C4+C5 complexes at various C4:C5 molar ratios from 2.3:1 to 2.6:1 exceeds the effect of DXR alone.

Example 12
The Anti-tumour Effect of DXR/C4+C5 Complexes, the C4:C5 Molar Ratios Being Equal to 2,7:1; 2.8:1; 2,9:1 and 3:1

Mice ICR of 20–22 g were inoculated intraperitoneally with $2\times10^6$ viable EAC cells. Starting two days later (day 2) mice were injected intravenously (in the volume of 2.5 ml/kg of body weight) once every other day, three times (day 2, 4 and 6). Mice of control group received vehicle. In the group of DXR mice received DXR alone in the dose of 3.5 mg/kg. Mice of first test group received the DXR/C4+C5 complex (C4:C5 molar ratio was equal to 2.7:1). Mice of second test group received the DXR/C4+C5 complex (C4:C5 molar ratio was equal to 2.8:1). Mice of third test group received the DXR/C4+C5 complex (C4:C5 molar ratio was equal to 2.9:1). Mice of fourth test group received the DXR/C4+C5 complex (C4:C5 molar ratio was equal to 3:1). Two days later after the final treatment with test complexes mice were killed by cervical dislocation on day 8. Tumour cell number was counted and the extent of inhibition of EAC growth in mice was evaluated.

Mice of control group had $(721.3\pm76.4)\times10^6$ EAC cells in abdominal cavity. In group with DXR alone the number of tumour cells was $(503.8\pm64.5)\times10^6$ and EAC growth inhibition of 30.2%, p<0.05. In mice of first test group the number of tumour cells was $(312.7\pm79.6)\times10^6$ and EAC growth inhibition of 56.6%, p<0.002. In mice of second test group the number of tumour cells was $(324.5\pm72.8)\times10^6$ and EAC growth inhibition of 55.0%, p<0.002. In mice of third test group the number of tumor cells was $(357.9\pm75.3)\times10^6$ and EAC growth inhibition of 50.4%, p<0.01. In mice of fourth test group the number of tumour cells was $(394.6\pm67.7)\times10^6$ and EAC growth inhibition of 45.3%, p<0.01.

Thus, anti-tumour activity of DXR/C4+C5 complexes at various C4:C5 molar ratios from 2.7:1 to 3:1 exceeds the effect of DXR alone.

Example 13
The Anti-tumour Effect of DXR/C4+C9 Complexes, the C4:C9 Molar Ratios Being Equal to 1:1; 1:1.4; 1:1.8 and 1:2.3. DXR—3.5 mg/kg of Body Weight. C4—8.15 mg/kg of Body Weight Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C9 complex (C4:C9 molar ratio was equal to 1:1). Mice of second test group received the DXR/C4+C9 complex (C4:C9 molar ratio was equal to 1:1.4). Mice of third test group received the DXR/C4+C9 complex (C4:C9 molar ratio was equal to 1:1.8). Mice of fourth test group received the DXR/C4+C9 complex (C4:C9 molar ratio was equal to 1:2.3). Two days later after the final treatment with the test complexes mice were killed by cervical dislocation on day 8. Tumour cell number was counted and the extent of inhibition of EAC growth in mice was evaluated.

Mice of control group had $(696.7\pm68.2)\times10^6$ EAC cells in abdominal cavity. In group with DXR alone the number of tumour cells was $(449.4\pm77.1)\times10^6$ and EAC growth inhibition of 35.5%, $p<0.05$. In mice of first test group the number of tumour cells was $(266.1\pm97.9)\times10^6$ and EAC growth inhibition of 61.8%, $p<0.01$. In mice of second test group the number of tumour cells was $(227.8\pm69.1)\times10^6$ and EAC growth inhibition of 67.3%, $p<0.001$, and with reference to DXR group (positive control) EAC growth inhibition of 49.3%, $p<0.05$. In mice of third test group the number of tumour cells was $(261.0\pm101.2)\times10^6$ and EAC growth inhibition of 62.5%, $p<0.01$. In mice of fourth test group the number of tumour cells was $(350.4\pm103.7)\times10^6$ and EAC growth inhibition of 49.7%, $p<0.02$.

Thus, the anti-tumour activity of DXR/C4+C9 complexes at C4:C9 molar ratios 1:1; 1:1.4; 1:1.8 and 1:2.3 exceeds the effect of DXR alone.

Example 14
Anti-tumour Effect of DXR/C4+C13 Complexes. C4:C13 Molar Ratios were Equal to 1:1.3; 1:1.6; 1:2 and 1:2.5. DXR—3.5 mg/kg of Body Weight. C4—8.15 mg/kg of Body Weight Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C13 complex (C4:C13 molar ratio was equal to 1:1.3). Mice of second test group received the DXR/C4+C13 complex (C4:C13 molar ratio was equal to 1:1.6). Mice of third test group received the DXR/C4+C13 complex (C4:C13 molar ratio was equal to 1:2). Mice of fourth test group received the DXR/C4+C13 complex (C4:C13 molar ratio was equal to 1:2.5). Two days later after the final treatment with the test complexes mice were killed by cervical dislocation on day 8. Tumour cell number was counted and the extent of inhibition of EAC growth in mice was evaluated.

Mice of control group had $(645.8\pm62.5)\times10^6$ EAC cells in abdominal cavity. In group with DXR alone the number of tumour cells was $(406.7\pm60.1)\times10^6$ and EAC growth inhibition of 37.0%, $p<0.05$. In mice of first test group the number of tumour cells was $(213.1\pm53.0)\times10^6$ and EAC growth inhibition of 67.0%, $p<0.001$, and with reference to DXR group (positive control) EAC growth inhibition of 47.6%, $p<0.05$. In mice of second test group the number of tumour cells was $(228.6\pm57.0)\times10^6$ and EAC growth inhibition of 64.6%, $p<0.001$ and with reference to DXR group (positive control) EAC growth inhibition of 43.8%, $p<0.05$. In mice of third test group the number of tumour cells was $(295.8\pm94.0)\times10^6$ and EAC growth inhibition of 54.2%, $p<0.01$. In mice of fourth test group the number of tumour cells was $(354.5\pm75.6)\times10^6$ and EAC growth inhibition of 45.1%, $p<0.01$.

Thus, anti-tumour activity of DXR/C4+C13 complexes at C4:C13 molar ratios 1:1.3; 1:1.6; 1:2 and 1:2.5 exceeds the effect of DXR alone.

Example 15
Anti-tumour Effect of DXR/C4+C17 Complexes. C4:C17 Molar Ratios were Equal to 1:1; 1.4:1; 2:1 and 2.7:1. DXR—3.5 mg/kg of Body Weight. C17—6.0 mg/kg of Body Weight Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4+C17 complex (C4:C17 molar ratio was equal to 1:1). Mice of second test group received the DXR/C4+C17 complex (C4:C17 molar ratio was equal to 1.4:1). Mice of third test group received the DXR/C4+C17 complex (C4:C17 molar ratio was equal to 2:1). Mice of fourth test group received the DXR/C4+C17 complex (C4:C17 molar ratio was equal to 2.7:1). Two days later after the final treatment with the test complexes mice were killed by cervical dislocation on day 8. Tumour cell number was counted and the extent of inhibition of EAC growth in mice was evaluated.

Mice of control group had $(834.9\pm71.1)\times10^6$ EAC cells in abdominal cavity. In group with DXR alone the number of tumour cells was $(495.1\pm68.0)\times10^6$ and EAC growth inhibition of 40.7%, $p<0.01$. In mice of first test group the number of tumour cells was $(309.7\pm71.7)\times10^6$ and EAC growth inhibition of 62.9%, $p<0.001$. In mice of second test group the number of tumour cells was $(272.2\pm68.5)\times10^6$ and EAC growth inhibition of 67.4%, $p<0.001$, and with reference to DXR group (positive control) EAC growth inhibition of 45.0%, $p<0.05$. In mice of third test group the number of tumour cells was $(331.5\pm74.8)\times10^6$ and EAC growth inhibition of 60.3%, $p<0.001$. In mice of fourth test group the number of tumour cells was $(402.4\pm83.9)\times10^6$ and EAC growth inhibition of 51.8%, $p<0.002$.

Thus, the anti-tumour activity of DXR/C4+C17 complexes at C4:C17 molar ratios 1:1; 1.4:1; 2:1 and 2.7:1 exceeds the effect of DXR alone.

Example 16
Anti-tumour Effect of DXR/C4a+C5 Complexes. C4a:C5 Molar Ratios were Equal to 1.2:1; 1.6:1; 1.9:1 and 2.5:1. DXR—3.5 mg/kg of Body Weight. C5—6.4 mg/kg of Body Weight Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/C4a+C5 complex (C4a:C5 molar ratio was equal to 1.2:1). Mice of second test group received the DXR/C4a+C5 complex (C4a:C5 molar ratio was equal to 1.6:1). Mice of third test group received the DXR/C4a+C5 complex (C4a:C5 molar ratio was equal to 1.9:1). Mice of fourth test group received the DXR/C4a+C5 complex (C4a:C5 molar ratio was equal to 2.5:1). Two days later after the final treatment with the test complexes mice were killed by cervical dislocation on day 8. Tumour cell number was counted and the extent of inhibition of EAC growth in mice was evaluated.

Mice of control group had $(811.3\pm73.8)\times10^6$ EAC cells in abdominal cavity. In group with DXR alone the number of tumour cells was $(442.2\pm51.5)\times10^6$ and EAC growth inhibition of 45.5%, $p<0.001$. In mice of first test group the number of tumour cells was $(288.8\pm89.6)\times10^6$ and EAC growth inhibition of 64.4%, $p<0.001$. In mice of second test group the number of tumour cells was $(223.9\pm68.8)\times10^6$ and EAC growth inhibition of 72.4%, $p<0.001$, and with reference to DXR group (positive control) EAC growth inhibition of 49.4%, $p<0.05$. In mice of third test group the number of tumour cells was $(306.7\pm91.3)\times10^6$ and EAC growth inhibition of 62.2%, $p<0.001$. In mice of fourth test group the number of tumour cells was $(385.4\pm94.7)\times10^6$ and EAC growth inhibition of 52.5%, $p<0.01$.

Thus, anti-tumour activity of DXR/C4a+C5 complexes at C4a:C5 molar ratios 1.2:1; 1.6:1; 1.9:1 and 2.5:1 exceeds the effect of DXR alone.

Example 17
Synthesis of the N-Acyl-O-Phospho-2-Aminoethanol
Were Acyl is:
cis-5,8,11,14-eicosatetraenoyl (arachidonoyl) (5)
cis-4,7,10,13,16,19-docosahexaenoyl (9)
cis-5,8,11,14,17-eicosapentaenoyl (13)
cis-9,12,15-octadecatrienoyl (linolenoyl) (17)

Polyunsaturated acid (1 mmol) and triethylamine (142 $\mu$l, 1,02 mmol) were dissolved in 2 ml of dry tetrahydrofuran, then dry acetonitrile (4 ml) was added, the mixture chilled to $-15°$ C., and 131 $\mu$l (1.02 mmol) of butyl chloroformate was added. After 30 min, the mixture free of the precipitated triethylamine hydrochloride was pipetted in a solution of O-phosphorylethanolamine ("Sigma-Aldrich") (212 mg, 1,5 mmol) in 3 ml of 1M $Na_2CO_3$ and 3 ml of $H_2O$. The mixture obtained was stirred for 1 h at 20–25° C., acidified with 1M HCl to pH 2–3 and extracted with chloroform-methanol (2:1, v/v). The extract was washed with methanol-water (10:9, v/v), concentrated under reduced pressure and dissolved in chloroform-methanol-$NH_3$ aq (13:5:1, v/v/v). The solution obtained was evaporated under reduced pressure and dissolved in ethanol-water (2:3, v/v, 15 ml). The emulsion obtained was washed with ether (2×10 ml) and evaporated under reduced pressure gave the ammonium salt of N-acyl-O-phospho-2-aminoethanol.

Yields: 84% (5); 88% (9); 83% (13); 73% (17).

All the products obtained are identical to the compounds prepared by the method using β-cyanoethyl phosphate for phosphorylation of the N-acyl derivatives.

For $^1$H-NMR-spectra ammonium salts were converted into acidified forms by means of washing of the chloroform-methanol (2:1, v/v) solutions with 1M HCl.

Example 18
Synthesis of The N-Retinoil-O-Phospho-L-Tyrosine
Were Retinoyl is:
all-trans-Retinoyl (4)
13-cis-Retinoyl (4a)

Retinoic acid (1 mmol) and triethylamine (142 $\mu$l, 1,02 mmol) were dissolved in 6 ml of tetrahydrofuran, the mixture chilled to $-15°$ C., and 131 $\mu$l (1.02 mmol) of butyl chloroformate was added. After 30 min, the mixture was added to the solution of 261 mg (1 mmol) of O-phospho-L-tyrosine ("Sigma-Aldrich") in 3 ml of 1M $Na_2CO_3$ and 3 ml of $H_2O$ Then 3 ml of EtOH was added. The mixture obtained was stirred for 4 h at 20–25° C., acidified with 1M HCl to pH 2–3 and extracted with chloroform-methanol (2:1, v/v). The extract was washed with methanol-water (10:9, v/v), concentrated under reduced pressure and dissolved in chloroform-methanol-$NH_3$ aq (13:5:1, v/v/v). The solution obtained was evaporated under reduced pressure and dissolved in ethanol-water (2:3, v/v, 15 ml). The emulsion obtained was washed with ether (5×10 ml) and evaporated under reduced pressure gave the ammonium salt of N-retinoyl-O-phospho-L-tyrosine.

Yields: 52% (4); 49% (4a).

All the products obtained are identical to the compounds prepared by the method using β-cyanoethyl phosphate for phosphorylation of the N-acyl derivatives.

For $^1$H-NMR-spectra ammonium salts were converted into acidified forms by means of washing of the chloroform-methanol (2:1, v/v) solutions with 1M HCl.

The present invention further concerns therapeutically useful compounds and the use of the same for the treatment of cancer. The invention also relates to the synthesis of amides of all-trans-retinoic acid and 13-cis-retinoic acid with doxorubicin having the following structures:

1. N-(all-trans-retinoyl)-doxorubicin

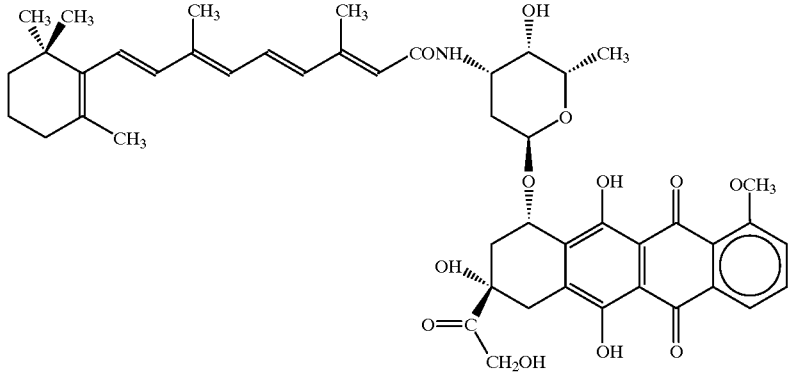

2. N-(13-cis-retinoyl)doxorubicin

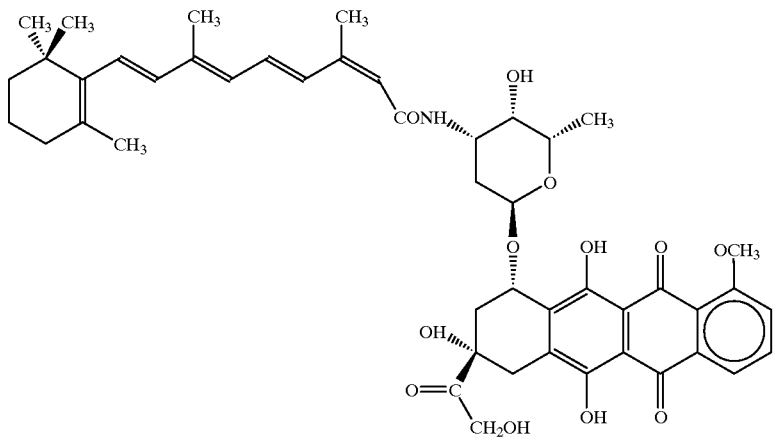

It is known that usefulness of natural retinoids for chemoprevention is limited by their toxicity. Synthetic retinamides that possess chemopreventive activity are less toxic then the natural retinoids (Shealy Y. F., et al., J. Med. Chem. V.31., P. 190–196, 1988). The title compounds could reveal not only the higher cytotoxicity to tumor cells, but a marked diminution in the toxicity of its preparations.

Our experimental results indicate that compound 1 reveals higher antitumor activity concerning Ehrlich ascites carcinoma (EAC), passed in C3H mice. Antitumor effect of compound 1 was dose-dependent. It is evidently, that compound 1 possess higher activity then that free doxorubicin at equivalent dose. Injection of compound 1 at the dose 50 mcg/mouse (2,5 mcg/kg) inhibited tumor growth by 57% while free doxorubicin at the same dose inhibited EAC growth by 45%.

The higher cytotoxic effects the conjugates of polyunsaturated fatty acids with daunomicin to AFP-generating rat hepatoma cells could be due to high affinity of AFP to arahidonic and docosahexaenoic acids. The complex AFP with fatty acids, modified by daunomicin, was delivered to AFP-generating rat hepatoma cells, selectively.

Non AFP-producing EAC was used in our experiments. It is established that reduce of antitumor activity of compound 1 is caused by the presence of that protein (AFP) in the preparations, which were used for injections to mice. The result of these experiments could be interpreted as a presence an equilibrium reversible complex formed between AFP and retinoic acid, modified by doxorubicin. Thus higher cytotoxic activity of compound 1, in comparison with doxorubicin, could be due to its structural peculiarities. The compound 1 include two antitumor agens—amide of retinoic acids and doxorubicin.

Example 19
Synthesis of N-(all-trans-retinoyl)-doxorubicin (compound 1)

all-trans-Retinoic acid (300 mg, 1 mmol) and triethylamine (104 mg, 1.02 mmol) were dissolved in 1 ml of dry tetrahydrofluran, then dry acetonitrile (4 ml) was added, and the mixture chilled to −15° C. Then 140 mg (1.02 mmol) of butyl chloroformate was added. After 30 min, the mixture free of the precipitated triethylamine hydrochloride was pipetted in a stirred suspension of Doxolem preparation containing 400 mg of doxorubicin hydrochloride and 2 g of lactose in a mixture of 1 ml of methanol and 0.1 ml triethylamine, stirring was continued for 15 min at −15° C., then the mixture obtained was allowed to warm to room temperature. After the mixture had stirred at room temperature under argon for 2 h, it was treated with 20 ml of benzene-ethanol (4:1). The suspension was centrifuged for 5 min at 3000 rpm, and the precipitate was treated with 20 ml of benzene-ethanol (4:1) and harvested by centrifigation (5 min, 3000 rpm). The two supernatants obtained were combined and evaporated to dryness in vacuo. The residue was dissolved in chloroform, and N-all-trans-retinoyl)-doxorubicin was purified by flash chromatography on silica gel (230–400 mesh). The column was eluted successively with chloroform, acetone-chloroform (1:9, v/v), acetone-chloroform (1:4, v/v) and finally with benzene-ethanol (4:1). The pure product was eluted with benzene-ethanol (4:1) as a deep-red band. The solvent was evaporated in vacuo to give 445 mg (78%) of N-(all-trans-retinoyl)-doxorubicin as a deep-red wax; TLC (benzene-dioxan-acetic acid 10:5:1) $R_f$ 0.5 (for doxorubicine 0.08); UV (ethanol) $A^{0.1\%}(345$ nm)= 817; $A^{0.1\%}$ (497 nm)=196; $^1$H-NMR (CDCl$_3$, 200 MHz) δ 0.9–1.0 (t and s, 6H, 3 CH$_2$ ring in retinoic acid), 1.2–1.3 (d, 3H, CH$_3$-5'), 1.4–2.4 (m, 19H, 5CH$_3$-RA, CH$_2$-2' and CH$_2$-8), 2.9–3.3 (q, 2H, CH$_2$-10), 3.7 (s, 1H, H-4'), 3.9–4.3 (m, 6H, OH-4', OCH$_3$, H-3', H-5'), 4.6 (s, 1H, COCH$_2$OH), 4.8 (s, 2H, COCH$_2$OH), 5.0–5.1 (d, 1H, OH-9), 5.3 (s, 1H, H-7), 5.5 (s, 1H, H-1'), 5.6–7.0 (m, 7H, 6HC=C-RA and NH), 7.3–7.4 (d, 1H, H-3), 7.7–7.8 (t, 1H, H-2), 8.0–8.1 (d, 1H, H-1), 13.1 and 14.0 (two s, 2H, OH-6 and OH-11)

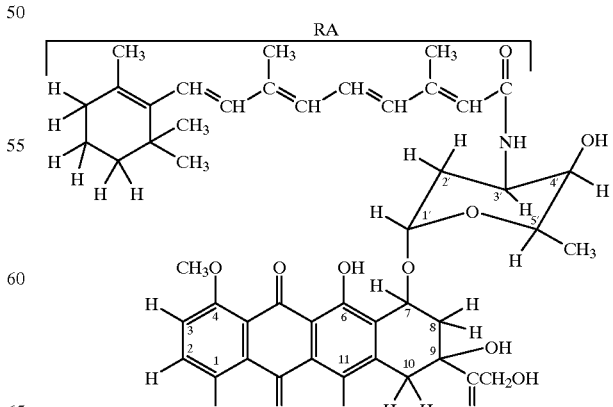

Example 20
The Antitumor Effect of N-(all-trans-retinoyl)-doxorubicin (compound 1) on EAC Cells A study of the anti-tumour effect of compound 1 as compared with doxorubicin was carried out in EAC, passed in C3H mice. 20–22 g males of C3H mice were used. Control and experimental groups included 7 animals, which were inoculated $5 \times 10^6$ EAC cells i.p. in volume 0.2 ml at day 0. On second, fourth and sixth days following inoculation the doses of 20, 50 and 100 µg/mouse of compound 1, equivalent ones of doxorubicin, in 200 µl of normal mice serum (NMS) were injected i.v. Three groups of animals were administrated water solutions of doxorubicin in doses of 1, 2.5 and 5 µg/kg of body weight (20, 50 and 100 µg/mouse by weight of 20 g accordingly). One group of mice was untreated control. Results of experiment were accounted on ninth day. Mice were killed by cervical dislocation. Ascitic fluids were removed, collected, their volumes were measured, and abdominal cavities were washed by saline solution 6–7 times. Thus obtained fluids were pooled. The number of viable tumor cells was counted by hemocytometer, using trypan blue exclusion test. The mean and the standard mean error was calculated for each group of mice. Comparison of tumor cell number in control and experimental groups was carried out using Student t-test. Influence of tested preparation on EAC growth inhibition was evaluated by:

$$\text{Inhibition, \%} = \frac{\text{Control} - \text{Experiment}}{\text{Control}} \times 100$$

The experimental results as shown in Table 1 indicate that compound 1 displays high antitumor activity towards EAC. The anti-tumour effect of compound 1 is dose-dependent. Injection of compound 1 three times repeatedly on the second, fourth and sixth days following inoculation in dose of 1 mg/kg (20 µg/mouse) gives an EAC growth inhibition of 47% as compared with control untreated animals (p<0.01). It is evident, that compound 1 possess a higher activity than that of free doxorubicin in an equivalent dose. In case of compound 1 injection in dose of 2.5 mg/kg (50 µg/mouse) according to taken scheme the tumour growth inhibition reached to 56% (p<0.01) while free doxorubicin at the same dose inhibited EAC growth of 45% (p<0.01). The smaller effect (EAC growth inhibition of 53%) was obtained in case of injection compound 1 at dose equivalent to 5 mg/kg (100 µg/mouse) of doxorubicin. It is seen, that the cytotoxic effect of free doxorubicin at this dose is the higher than that of compound 1.

Thus, the experiment shows that compound 1 at doses, corresponding to 1 and 2.5 mg/kg of doxorubicin, exerts high anti-tumour effect towards EAC, and further, that the cytotoxicity of compound 1 is the higher than that of free doxorubicin.

TABLE 1

Antitumor effect of compound 1 and doxorubicin at three times repeated i.v injections to mice with EAC (M ± m, n = 7)

| Group of animals | Preparation | Dose, µg/mouse, i.v. | Ascites volume, ml | Tumor cell quantity, × $10^6$ | EAC growth inhibition, % to control | P |
|---|---|---|---|---|---|---|
| Control | Untreated | — | 5.05 ± 0.85 | 1213.6 ± 137.96 | — | — |
| Experiment 1 | Compound 1 | 20 | 3.50 ± 1.30 | 640.0 ± 78.04 | 47.3 | <0.01 |
| Experiment 2 | Doxorubicin | 20 | 2.85 ± 1.35 | 765.8 ± 127.52 | 36.9 | <0.05 |
| Experiment 3 | Compound 1 | 50 | 2.10 ± 1.70 | 535.0 ± 167.90 | 55.9 | <0.01 |
| Experiment 4 | Doxorubicin | 50 | 1.85 ± 1.10 | 662.1 ± 99.17 | 45.4 | <0.01 |
| Experiment 5 | Compound 1 | 100 | 3.30 ± 1.20 | 571.4 ± 66.96 | 52.9 | <0.002 |
| Experiment 6 | Doxorubicin | 100 | 0.80 ± 0.60 | 350.0 ± 108.21 | 71.2 | <0.001 |

Example 21
Effect of N-(all-trans-retinoyl)-doxorubicin (compound 1) with AFP on Growth of EAC in Mice The influence of compound 1 with different amount of AFP on the growth of EAC was studied. The experiments were carried out on inbred C3H mice having initial weight of 20–23 g. The used tumor cell strain was supported by i.p. passages to mice of the same line. At the beginning of the research (day 0) four groups, each of which contained 7 mice, were formed. All of the animals were inoculated by tumour cells in saline solution i.p. ($5 \cdot 10^6$ cells in 0,2 ml per a mouse).

The injections of different preparations of compound 1 and doxorubicin with AFP were carried out on second, fourth and sixth days after i.p. implantation of EAC cells to mice. The first group of animals was untreated (negative control). The mice were injected by NMS. The mice of second group were injected by compound 1 containing doxorubicin in the dose of 1 µg/kg of body weight (20 µg/mouse) i.v., NMS being used as solvent. The animals of third and fourth groups were injected the same dose of compound 1, the protein being added to NMS (2,5 and 5 µg/mouse, accordingly). On the ninth day after inoculation by EAC cells the mice were killed and ascitic fluids were collected and estimated quantitatively. Tumor cells suspensions were prepared and aliquotes were mixed with equal volume of 0,1% trypan blue solution. The quantity of tumor cells were counted with hemocytometer.

Results of the experiments were evaluated by means of variation statistics method using Student t-test. The values of inhibiting effects of the preparations were represented as percentage in comparison with control.

As seen from presented data of experiment (Table 2) compound 1 in dose of 1 mg/kg (20 µg/mouse) inhibits the EAC growth of 45% (p<0,01). This is in concordance with data of previous experiment. In the same time the influence of compound 1 (20 µg/mouse), loaded by AFP (2,5 µg/mouse), is lowered up to 33% (p<0,01) of tumor growth inhibition. Antitumor effect value of compound 1 with double content of AFP in injected solution (31%, p<0,02) is not changed essentially. It is seen that effect of compound 1 with AFP (2,5 and 5,0 μg/mouse) is near to one of free doxorubicin.

TABLE 2

Effect of compound 1 in the dose of 1 mg/kg (20 μg/mouse) with AFP at three times repeated i.v. injections to mice C3H on growth of EAC (M ± m, n = 7)

| Treatment | Dose of AFP, μg/mouse | Ascites volume, ml | Tumor cell quantity, × $10^6$ | EAC growth inhibition, % to control | p |
|---|---|---|---|---|---|
| 1. NMS | None | 3.4 ± 1.01 | 2157.8 ± 207.6 | — | — |
| 2. Compound 1 | None | 2.0 ± 0.25 | 1185.7 ± 266.2 | 45.0 | <0.01 |
| 3. Compound 1 + AFP | 2.5 | 3.0 ± 0.60 | 1442.9 ± 108.3 | 33.1 | <0.01 |
| 4. Compound 1 + AFP | 5.0 | 2.8 ± 0.65 | 1481.4 ± 171.3 | 31.3 | <0.02 |
| 5. Doxorubicin | None | — | — | 36.9* | <0.01 |

*see Table 1.

Example 22
The Anti-tumour Effect of N-(13-cis-retinoyl)-doxorubicin (compound 2) on Growth of EAC in Mice Mice C3H of 20–22 g were inoculated intraperitoneally with $2 \times 10^6$ viable EAC cells. Starting two days later (day 2) mice were injected intravenously (in the volume of 10 ml/kg of body weight or 200 μl/mouse by weight of 20 g) once every other day, three times (day 2, 4 and 6). Mice of control group received NMS. In two groups of doxorubicin (positive controls) mice received doxorubicin alone (in NMS) in doses of 1 or 2.5 mg/kg of body weight (20 or 50 μg/mouse by weight of 20 g) accordingly. Mice of two test groups received the compound 2 in NMS, containing doxorubicin in doses of 1 or 2.5 mg/kg of body weight (20 or 50 μg/mouse by weight of 20 g) accordingly. Three days later after the final treatment with test compound mice were killed by cervical dislocation on day 9. Tumour cell number was counted and the extent of inhibition of EAC growth in mice was evaluated.

Mice of control group had $(975.4 \pm 81.37) \times 10^6$ EAC cells in abdominal cavity. In the group with doxorubicin alone in the dose of 1 mg/kg the number of tumour cells was $(635.9 \pm 122.78) \times 10^6$ and EAC growth inhibition of 34.8%, p<0.05. In mice of test group with compound 2, containing doxorubicin in doses of 1 mg/kg, the number of tumour cells was $(533.5 \pm 94.23) \times 10^6$ and EAC growth inhibition of 45.3%, p<0.01. In the group with doxorubicin alone in the dose of 2.5 mg/kg the number of tumour cells was $(537.4 \pm 92.89) \times 10^6$ and EAC growth inhibition of 44.9%, p<0.01. In mice of test group with compound 2, containing doxorubicin in doses of 2.5 mg/kg, the number of tumour cells was $(405.7 \pm 120.62) \times 10^6$ and EAC growth inhibition of 58.4%, p<0.002.

Thus, the compound 2 in doses, corresponding to 1 and 2.5 mg/kg of doxorubicin, exerts high antitumor effect in respect to EAC, exceeding the effect of doxorubicin alone.

Example 23
Synthesis of the N-(13-cis-Retinoyl)-Doxorubicin/ Compound 2/

This compound was prepared as described above for compound 1, using 1 mmol (300 mg) of 13-cis-Retinoic acid; yield 429 mg (75%).

TLC (benzene-dioxan-acetic acid 10:5:1) $R_f$ 0.5 (for doxorubicin 0.08); UV (ethanol) $A^{0.1\%}$ (347 nm)=817; $A^{0.1\%}$ (497 nm)=196; $^1$H-NMR (CDCl$_3$, 200 MHz) δ 0.9–1.0 (t and s, 6H, 3 CH$_2$ ring in retinoic acid), 1,2–2,4 (m, 22H, CH$_3$-5', 5 CH$_3$-RA, CH$_2$-2' and CH$_2$-8), 2.9–3.3 (q, 2H, CH$_2$-10), 3.7 (s, 1H, H-4'), 3.9–4.3 (m, 6H, OH-4', OCH$_3$, H-3', H-5'), 4.6 (s, 1H, COCH$_2$OH), 4.8 (s, 2H, COCH$_2$OH), 5.0–5.1 (d, 1H, OH-9), 5.3 (s, 1H, H-7), 5.5 (s, 1H, H-1'), 5.6–7.0 (m, 7H, 6HC=C-RA and NH), 7.3–7.4 (d, 1H, H-3), 7.7–7.8 (t, 1H, H-2), 8.0–8.1 (d, 1H, H-1), 13.1 and 14.0 (two s, 2H, OH-6 and OH-11).

Example 24
Anti-tumour Effect of DXR/(C4+C4a)+C5 Complexes (C4+C4a):C5 molar ratios were equal to 1.2:1; 1.6:1; 1.9:1 and 2.5:1. C4:C4a molar ratio was equal to 3:2. DXR—3.5 mg/kg of body weight. C5—6.4 mg/kg of body weight.

Mice ICR of 20–22 g were inoculated intraperitoneally with $2 \times 10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/(C4+C4a)+C5 complex. (C4+C4a):C5 molar ratio was equal to 1.2:1. Mice of second test group received the DXR/(C4+C4a)+C5 complex. (C4+C4a):C5 molar ratio was equal to 1.6:1. Mice of third test group received the DXR/(C4+C4a)+C5 complex. (C4+C4a):C5 molar ratio was equal to 1.9:1. Mice of fourth test group received the DXR/(C4+C4a)+C5 complex. (C4+C4a):C5 molar ratio was equal to 2.5:1. Two days later after the final treatment with the test complexes mice were killed by cervical dislocation on day 8. Tumour cell number was counted and the extent of inhibition of EAC growth in mice was evaluated.

Mice of control group had $(768.7 \pm 102.8) \times 10^6$ EAC cells in abdominal cavity. In group with DXR alone the number of tumour cells was $(465.1 \pm 62.8) \times 10^6$ and EAC growth inhibition of 39.5%, p<0.05. In mice of first test group the number of tumour cells was $(283.6 \pm 71.4) \times 10^6$ and EAC growth inhibition of 63.1%, p<0.002. In mice of second test group the number of tumour cells was $(218.3 \pm 65.3) \times 10^6$ and EAC growth inhibition of 71.6%, p<0.001, and with reference to DXR group (positive control) EAC growth inhibition of 53.1%, p<0.02. In mice of third test group the number of tumour cells was $(299.7 \pm 73.6) \times 10^6$ and EAC growth inhibition of 61.0%, p<0.002. In mice of fourth test group the number of tumour cells was $(405.1 \pm 81.5) \times 10^6$ and EAC growth inhibition of 47.3%, p<0.02.

Thus, antitumour activity of DXR/(C4+C4a)+C5 complexes at (C4+C4a):C5 molar ratios 1.2:1; 1.6:1; 1.9:1 and 2.5:1 exceeds the effect of DXR alone.

Example 25
Anti-tumour Effect of DXR/(C4+C4a)+(C5+C9+C13) Complexes (C4+C4a):(C5+C9+C13) molar ratios were equal to 1:1; 1:1.4; 1:1.8 and 1:2.3. C4:C4a molar ratio was equal to 2:3. C5:C9:C13 molar ratios were equal to 0.5:1:1. DXR—3.5 mg/kg of body weight. (C4+C4a)—8.15 mg/kg of body weight.

Mice ICR of 20–22 g were inoculated intraperitoneally with $2 \times 10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/(C4+C4a)+(C5+C9+C13) complex. (C4+C4a):(C5+C9+C13) molar ratio was equal to 1:1. Mice of second test group received the DXR/(C4+C4a)+(C5+C9+C13) complex. (C4+C4a):(C5+C9+C13) molar ratio was equal to 1:1.4. Mice of third test group received the DXR/(C4+C4a)+(C5+C9+C13) complex. (C4+C4a):(C5+C9+C13) molar ratio was equal to 1:1.8. Mice of fourth test group received the DXR/(C4+C4a)+(C5+C9+C13) complex. (C4+C4a):(C5+C9+C13) molar ratio was equal to 1:2.3). Two days later after the final treatment with the test complexes mice were killed by cervical dislocation on day 8. Tumour cell number was counted and the extent of inhibition of EAC growth in mice was evaluated.

Mice of control group had $(817.2\pm99.9)\times10^6$ EAC cells in abdominal cavity. In group with DXR alone the number of tumour cells was $(517.7\pm74.9)\times10^6$ and EAC growth inhibition of 36.9%, $p<0.05$. In mice of first test group the number of tumour cells was $(326.1\pm92.8)\times10^6$ and EAC growth inhibition of 60.1%, $p<0.01$. In mice of second test group the number of tumour cells was $(259.0\pm72.6)\times10^6$ and EAC growth inhibition of 68.3%, $p<0.001$, and with reference to DXR group (positive control) EAC growth inhibition of 49.8%, $p<0.05$. In mice of third test group the number of tumour cells was $(316.3\pm81.3)\times10^6$ and EAC growth inhibition of 61.3%, $p<0.002$. In mice of fourth test group the number of tumour cells was $(431.5\pm74.1)\times10^6$ and EAC growth inhibition of 47.2%, $p<0.01$.

Thus, the anti-tumour activity of DXR/(C4+C4a)+(C5+C9+C13) complexes at (C4+C4a):(C5+C9+C13) molar ratios 1:1; 1:1.4; 1:1.8 and 1:2.3 exceeds the effect of DXR alone.

Example 26
Antitumour Effect of DXR/(C4+C4a)+(C5+C9+C13+C17) Complexes (C4+C4a):(C5+C9+C13+C17) molar ratios were equal to 1:1.3; 1:1.6; 1:2 and 1:2.5. C4:C4a molar ratio was equal to 1:1. C5:C9:C13:C17 molar ratios were equal to 1:1:1:1. DXR—3.5 mg/kg of body weight. (C4+C4a)—8.15 mg/kg of body weight.

Mice ICR of 20–22 g were inoculated intraperitoneally with $2\times10^6$ viable EAC cells. Starting two days later (day 2) mice were injected intravenously (in the volume of 2.5 ml/kg body weight) once every other day, three times (day 2, 4 and 6). Mice of control group received vehicle. In the group of DXR mice received DXR alone in the dose of 3.5 mg/kg. Mice of first test group received the DXR/(C4+C4a)+(C5+C9+C13+C17) complex (C4+C4a):(C5+C9+C13+C17) molar ratio was equal to 1:1.3. Mice of second test group received the DXR/(C4+C4a)+(C5+C9+C13+C17) complex. (C4+C4a):(C5+C9+C13+C17) molar ratio was equal to 1:1.6. Mice of third test group received the DXR/(C4+C4a)+(C5+C9+C13+C17) complex (C4+C4a):(C5+C9+C13+C17) molar ratio was equal to 1:2. Mice of fourth test group received the DXR/(C4+C4a)+(C5+C9+C13+C17) complex (C4+C4a):(C5+C9+C13+C17) molar ratio was equal to 1:2.5. Two days later after the final treatment with the test complexes mice were killed by cervical dislocation on day 8.

Tumour cell number was counted and the extent of inhibition of EAC growth in mice was evaluated.

Mice of control group had $(738.1\pm73.9)\times10^6$ EAC cells in abdominal cavity. In group with DXR alone the number of tumour cells was $(431.1\pm57.4)\times10^6$ and EAC growth inhibition of 41.6%, $p<0.01$. In mice of first test group the number of tumour cells was $(235.9\pm65.1)\times10^6$ and EAC growth inhibition of 68.0%, $p<0.001$, and with reference to DXR group (positive control) EAC growth inhibition of 45.3%, $p<0.05$. In mice of second test group the number of tumour cells was $(223.7\pm70.3)\times10^6$ and EAC growth inhibition of 69.7%, $p<0.001$ and with reference to DXR group (positive control) EAC growth inhibition of 48.1%, $p<0.05$. In mice of third test group the number of tumour cells was $(322.6\pm88.5)\times10^6$ and EAC growth inhibition of 56.3%, $p<0.01$. In mice of fourth test group the number of tumour cells was $(417.2\pm69.7)\times10^6$ and EAC growth inhibition of 43.5%, $p<0.01$.

Thus, the anti-tumour activity of DXR/(C4+C4a)+(C5+C9+C13+C17) complexes at (C4+C4a):(C5+C9+C13+C17) molar ratios 1:1.3; 1:1.6; 1:2 and 1:2.5 exceeds the effect of DXR alone.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

What is claimed is:

1. A compound having the following formula:

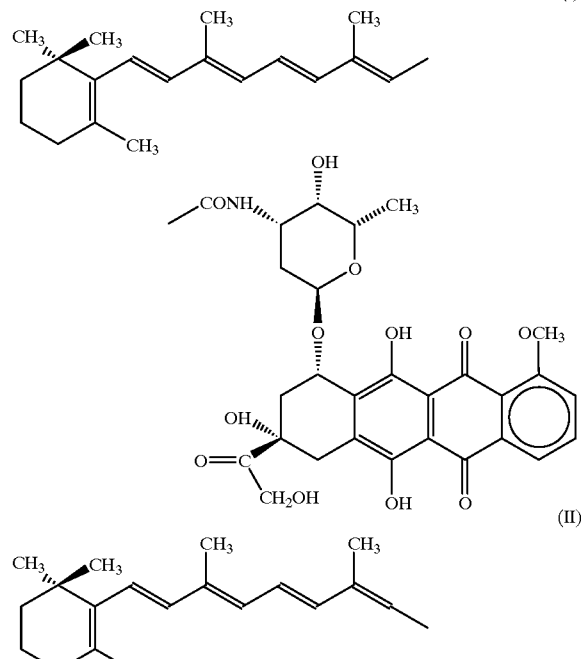

(I)

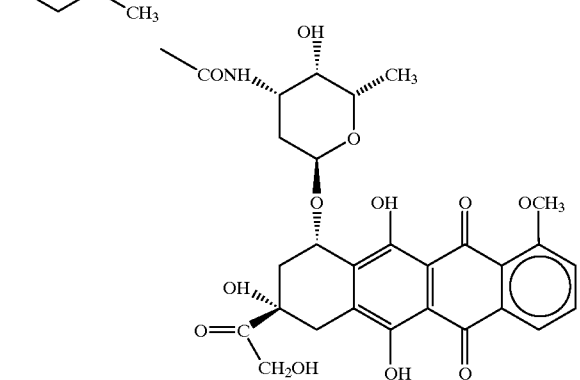

(II)

2. A method for the treatment of cancer, comprising administering N-(all trans-retinol)-doxorubicin(I) to a mammal.

3. A method for the treatment of cancer, comprising administering N-(13-cis-retinoyl)-dororubicin(II) to a mammal.

4. The method of claim 2 wherein N-(all trans-retinoyl)-doxorubicin(I) is administered intravenously.

5. The method of claim 3 wherein N-(13-cis-retinoyl)-doxorubicin(II) is administered intravenously.

* * * * *